(12) United States Patent
Zuñiga et al.

(10) Patent No.: US 11,357,737 B2
(45) Date of Patent: Jun. 14, 2022

(54) CHITOSAN NANOFIBERS CONTAINING BIOACTIVE COMPOUNDS

(71) Applicants: FUNDACION COPEC UNIVERSIDAD CATÓLICA, Santiago (CL); UNIVERSIDAD DE VALPARAISO, Valparaiso (CL)

(72) Inventors: Elisa Zuñiga, Santiago (CL); Pablo Muñoz, Valparaiso (CL); Osvaldo Rubilar, Santiago (CL)

(73) Assignees: FUNDACION COPEC UNIVERSIDAD CATOLICA, Santiago (CL); UNIVERSIDAD DE VALPARAISO, Valparaiso (CL)

( * ) Notice: Subject to any disclaimer, the term of this patent is extended or adjusted under 35 U.S.C. 154(b) by 480 days.

(21) Appl. No.: 15/579,886

(22) PCT Filed: Jun. 4, 2016

(86) PCT No.: PCT/CL2016/050030
§ 371 (c)(1),
(2) Date: Dec. 5, 2017

(87) PCT Pub. No.: WO2016/191895
PCT Pub. Date: Dec. 8, 2016

(65) Prior Publication Data
US 2018/0169031 A1 Jun. 21, 2018

(30) Foreign Application Priority Data
Jun. 5, 2015 (CL) .................... 1532-2015

(51) Int. Cl.
| | | |
|---|---|---|
| *A61K 9/70* | (2006.01) | |
| *A61K 31/722* | (2006.01) | |
| *A23L 33/10* | (2016.01) | |
| *A61P 25/28* | (2006.01) | |
| *A61K 9/00* | (2006.01) | |
| *A61K 31/192* | (2006.01) | |
| *A61K 31/353* | (2006.01) | |
| *A61K 31/366* | (2006.01) | |
| *A61K 31/375* | (2006.01) | |
| *A61K 47/36* | (2006.01) | |

(52) U.S. Cl.
CPC ............... *A61K 9/70* (2013.01); *A23L 33/10* (2016.08); *A61K 9/0053* (2013.01); *A61K 9/7007* (2013.01); *A61K 31/192* (2013.01); *A61K 31/353* (2013.01); *A61K 31/366* (2013.01); *A61K 31/375* (2013.01); *A61K 31/722* (2013.01); *A61K 47/36* (2013.01); *A61P 25/28* (2018.01); *A23V 2002/00* (2013.01)

(58) Field of Classification Search
USPC ........................................................ 424/443
See application file for complete search history.

(56) References Cited

U.S. PATENT DOCUMENTS

| | | | |
|---|---|---|---|
| 2003/0104020 A1* | 6/2003 | Davison | A61K 8/02 424/401 |
| 2006/0051423 A1 | 3/2006 | Heppe et al. | |
| 2017/0238569 A1* | 8/2017 | Adam | B65D 81/28 |

OTHER PUBLICATIONS

Mertens-Talcott et al. (The Journal of Nutrition, vol. 133, Issue 8, Aug. 2003, pp. 2669-2674). (Year: 2003).*
Jang et al. (J. Agric. Food Chem. 2008, 56, 1936-1941). (Year: 2008).*
Chitosan LMW 448869—Sigma-Aldrich Catalog obtained online (p. 1). (Year: 2019).*
Prado et al. (J. Therm. Anal. Calorim. (2011) 106:415-420). (Year: 2011).*
International Search Report for PCT/CL2016/050030 (dated Oct. 4, 2016).
Kim et al., "The inhibition of glioma growth in vitro and in vivo by a chitosan/ellagic acid composite biomaterial," Biomaterials, 30:4743-4751 (2009).
Kim, "Chitosan/Ellagic Acid Composite Materials for Local Cancer Therapy," A Dissertation presented for the Graduate Studies Council, The University of Tennessee, Health Science Center (2009) available at http://citeseerx.ist.psu.edu/viewdoc/download?doi=10.1.1.691.3913&rep=rep1&type=pdf.

* cited by examiner

*Primary Examiner* — Jessica Worsham
(74) *Attorney, Agent, or Firm* — Hamre, Schumann, Mueller & Larson, P.C.

(57) ABSTRACT

The invention relates to self-assembled nanofibers of chitosan and bioactive compounds for use as nutraceuticals or drugs. Suitable bioactive compounds include molecules of a low molecular size with acid or lactone groups, aromatic rings and hydroxyls. The nanofibers are absorbed, without degradation, in the small intestine, containing and protecting the bioactive compounds until they reach target organs. The nanofibers also cross the blood-brain barrier, allowing the compounds to reach the brain where they act as a controlled release system. If the bioactive compounds are neuroprotectors, the nanofibers can treat or prevent neurodegenerative diseases, strokes and other diseases related to aging or associated with oxidative stress. The invention also relates to a method for obtaining the nanofibers involving mixing chitosan with the bioactive compounds and allowing self-assembly. The invention further relates to a dosage form containing the nanofibers, particularly for oral administration.

14 Claims, 10 Drawing Sheets

FIG. 17 (a)
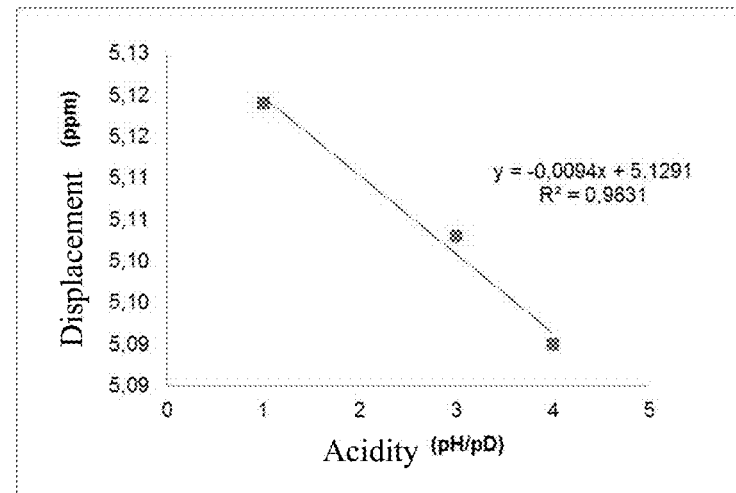
FIG. 17 (b)
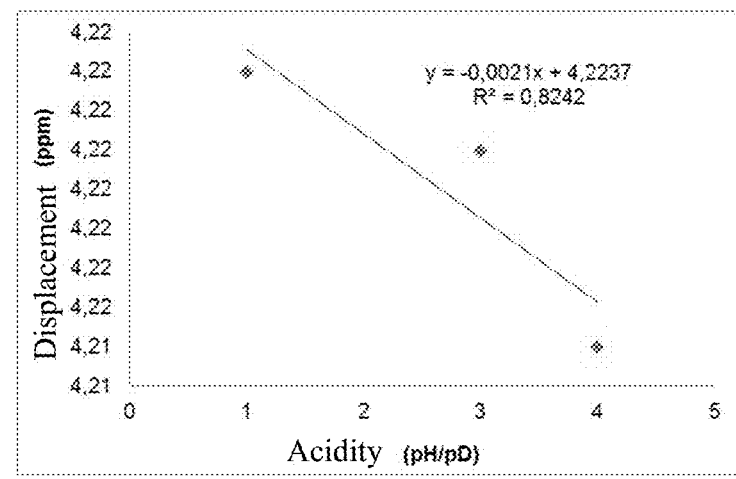
FIG. 17 (c)
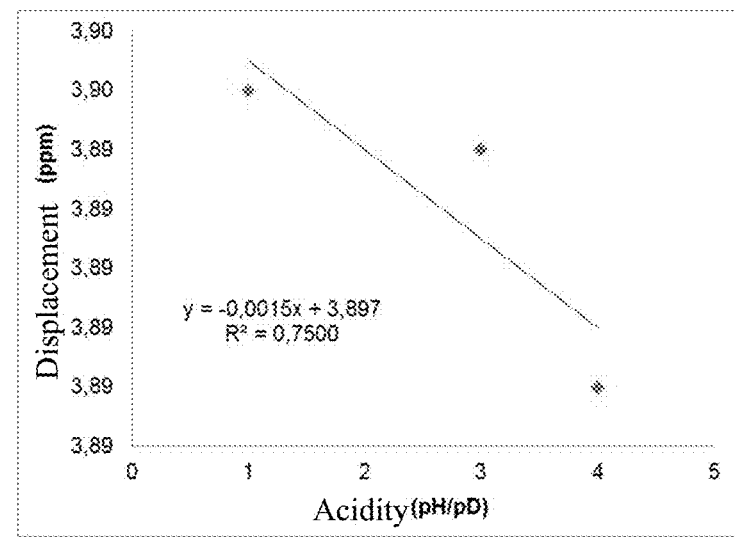
FIG. 17

CHITOSAN NANOFIBERS CONTAINING BIOACTIVE COMPOUNDS

This application is a U.S. National Stage Application under 35 U.S.C. § 371 of International Patent Application No. PCT/CL2016/050030 filed Jun. 4, 2016, which claims the benefit of priority to Chilean Patent Application No. 1532-2015 filed Jun. 5, 2015, the disclosures of all of which are hereby incorporated by reference in their entireties. The International Application was published in Spanish on Dec. 8, 2016 as WO 2016/191895.

DESCRIPTION

Technical Field of the Invention

The invention relates to self-assembled chitosan nanofibers containing bioactive, biodegradable and safe compounds, useful as nutraceuticals or drugs.

These nanofibers are absorbed mainly in the small intestine and cross the blood-brain barrier increasing the bioavailability of bioactive compounds in different organs, including the brain, where it acts as a controlled release system (CRS). Nanofibers containing bioactive antioxidant compounds are especially useful in the treatment or prevention of neurodegenerative diseases, such as Alzheimer's, Parkinson's, Huntington's, Amyotrophic Lateral Sclerosis (ALS); as well as Ischaemic Strokes and other diseases related to aging or associated with oxidative stress.

Background of the Invention

As indicated, the invention relates to nanofibers constituted by chitosan as a container of bioactive compounds, where the nanofiber is self-assembled, biodegradable, acts as a controlled release system (CRS) and is useful as a nutraceutical or drug.

The first component of nanofibers is chitosan, which is a linear polysaccharide composed of randomly distributed $\beta$-(1→4)-D-glucosamine and $\beta$-(1→4)-N-acetyl-D-glucosamine units. Commercially, it is produced by deacetylation of chitin, a structural polysaccharide present in fungi, in the exoskeleton of crustaceans and insects, which is the most abundant natural biopolymer after cellulose.

Chitin and chitosan form a family of biopolymers with different degrees of deacetylation, this parameter is the difference between being in the presence of chitin or chitosan itself, defining the latter as a product with a degree of deacetylation of chitin greater than 60%.

Chitosan is different from other commonly available polysaccharides, due to the presence of nitrogen as a protonated amino group ($-NH_3^+$) in its molecular structure, which confers positive charge and a capacity for polyelectrolyte complex formation. The cationic nature of the polymer allows it to be soluble in water or to form salts with negatively charged groups, such as carboxylates or hydroxyls (hydroxylates). In addition, it can form cross-linked gels with polymeric materials that exhibit anionic charges (Bhattarai et al., 2010, Chitosan-based hydrogels for controlled, localized drug delivery, Advanced Drug Delivery Reviews, 62, 83-99). It is an excellent excipient, because it is not toxic, it is stable, biodegradable and can be sterilized. These properties also make chitosan a very versatile material with a wide application in the fields of biomedicine and biotechnology. Reasons why the inventors chose it to develop the nanofibers of the invention.

In the state of the art we find many nanoapplications of chitosan, both as nanofibers or as nanoparticles, which contain drugs, cells, proteins, nucleic acids, and other molecules. The most common systems described in patents and/or scientific articles include the derivatization of chitosan and/or the interaction with other anionic charge polymers to produce crosslinking between various chitosan chains.

The derivatization of chitosan involves a directed chemical synthesis, where in the first place reactive groups, such as for example: tri-phosphate and glutaraldehyde, are added to the functional groups of the chitosan molecules, to then crosslink them covalently, in a determined pattern, and form various nanostructures containing bioactive compounds. When performing this type of organic synthesis, organic solvents must be used, which are often incompatible with biomedical applications. Although both the crosslinkers and the solvents can be in small proportions, they are highly toxic, so they must be extracted from the final product and it must be proven that the product is free of these compounds, which increases the production costs thereof.

The nanofibers of the invention solve this technical problem, since they do not comprise covalent bonds between the chitosan and the bioactive compounds, so they do not require the formation of derivatives, nor are they produced by organic synthesis, whereby the nanofibers of the invention are safe for applications in drugs and nutraceuticals, since they do not contain any toxic waste.

The nanofibers of the invention, comprise chitosan and bioactive compounds, the latter correspond to molecules of low molecular size that have acid groups, lactones, aromatic rings, hydroxyl, such as small polyphenols and their mixtures, where most of the bioactive compounds of these characteristics present antioxidant capacity and/or other biological activities.

Despite the indisputable beneficial impact of bioactive compounds with antioxidant capacity in the diet, such as those naturally contained in fruits and vegetables, this is not always sufficient for the prevention or treatment of neurodegenerative or other diseases related to aging. The main reason is the low bioavailability of antioxidants, such as polyphenols, from the diet, since for a polyphenol or other antioxidant to be bioavailable, it must first resist the strongly acid medium of the stomach, the enzymatic degradation of the gastrointestinal tract (GIT) and the metabolic degradation of the varied microbiota inhabited by the GIT (Scheepens et al., 2010, Improving the oral bioavailability of beneficial polyphenols through designed synergies, Genes Nutr 5, 75-87) that may even be responsible for the destruction of its chemical nature, and therefore, its bioactivity. The maximum plasma concentration in humans rarely exceeds 1 μM after consumption of 10-100 mg of a single polyphenolic compound. There is a great amount of literature that shows the beneficial effects of both natural and synthetic antioxidants for the human organism, and in particular, for the central nervous system (CNS) and some of its diseases. However, to achieve sufficient concentration to produce an effect on the brain, the compounds consumed must also overcome the blood-brain barrier (BBB), which protects and isolates the brain and spinal cord from the rest of the body. The BBB is very selective in the passage of molecules, preventing the entry of more than 95% of xenobiotic molecules and almost all small peptides and proteins.

This barrier limits the use of antioxidant compounds, and many other drugs, as potential therapeutic agents, since to reach the appropriate concentrations in the brain it is necessary to administer or consume very high doses, with the risk of an overdose that can be translated in a pro-oxidant activity in other organs (Rahal et al., 2014, Oxidative Stress, Prooxidants, and Antioxidants: The Interplay, BioMed Research International).

To solve these difficulties the inventors have developed the nanofibers of the invention, a system formed with chitosan molecules that self-assemble in the form of nanofibers when the chitosan molecule interacts with the functional groups present in the bioactive compounds, acting as controlled release nanocontainers of these bioactive compounds.

Surprisingly, these new nanofibers present a greater bioavailability, are absorbed without degrading at the level of the small intestine and are able to cross the blood-brain barrier and to release controlled bioactive compounds in organs, for example, antioxidants in the brain. For this reason, the nanofiber system of the invention is useful for obtaining a medicament or a nutraceutical composition that serves for the administration of bioactive compounds, such as antioxidants, and in this way prevent or treat neurodegenerative or other diseases related to aging or oxidative stress. This nanofiber is especially useful in the treatment and prevention of neurodegenerative diseases, such as Alzheimer's, Parkinson's, Huntington's, Amyotrophic Lateral Sclerosis (ALS); as well as Ischaemic Strokes and other diseases related to aging or associated with oxidative stress.

In the state of the art we find numerous publications that disclose the use of chitosan in nanoparticles, nanofibers and as part of controlled release systems, even in controlled release systems that cross the BBB, however none anticipates the nanofibers of the invention.

For example, the international publication WO 2006/062 506 A1 refers to a liposome coated by chitosan for the delivery of antioxidant compounds. The antioxidants are in a proliposomal preparation coated with chitosan and the controlled release is given by a layer between the chitosan and the preparation with the active compounds. The sustained release layer is hydroxypropylmethylcellulose, polyethylene glycol or ethylcellulose. As can be seen, it is not the chitosan-antioxidant interaction that is fundamental in this composition and, additionally, it is not a nanocomposition.

Another publication that discloses the controlled release of active compounds from chitosan is the application US 2010/0093661 A1, wherein a chitosan conjugate is disclosed via formation of an amididic bond with a drug that has an acid group, which is reacted first to obtain an acid halide, an ester, an anhydrous or another intermediate product, for the final reaction with the chitosan that produces the formation of a conjugate. As explained above, this corresponds to a chemical derivatization of chitosan and is not related to the nanofiber of the invention.

The publication US 2006 051423 A1, indicates that it has a drug transport system to the brain, based on chitosan, where drugs can be antioxidants, covalently bound to chitosan; additionally the system is coated by starch, alginate or their mixtures. Therefore, the subject of US 2006 051423 A1 does not anticipate the nanofiber of the invention.

A publication that a priori appears as the closest to the present invention is by Pérez Quiñones (2012, Carbohydrate Polymers, 88, 1373-1377) Self-assembled nanoparticles of glycol chitosan—Ergocalciferol succinate conjugate, for controlled release; however, self-assembly of the particles occurs again by the formation of a covalent amide bond between the ergoscalciferol hemisuccinate activated by a carboimide, with the amino group of the chitosan. So this publication does not anticipate the nanofiber of the invention, where no covalent bonds are formed, but as we will see later, there are interactions of hydrogen bonds between the components.

Finally, the publication of Pasanphan and Chirachanchai (2010, Conjugation of Gallic acid onto chitosan: An approach for green and water-based antioxidant, Carbohydrate Polymers, 72, 169-177) also discloses the conjugation of chitosan with activated gallic acid by a carbodimide. Again, they refer to bonds by formation of covalent bonds, and therefore, it does not anticipate the nanofiber of the invention.

That is to say, there is no document in the prior art that, by itself or in combination with others, anticipates the invention.

DESCRIPTION OF THE FIGURES

FIG. 17. Displacement graph signals the hydrogen nuclei of ascorbic acid in the ascorbic chitosan system attached to the carbons (a) $C_4$, (b) $C_5$ and (c) $C_6$.

DETAILED DESCRIPTION OF THE INVENTION

Figure 1:
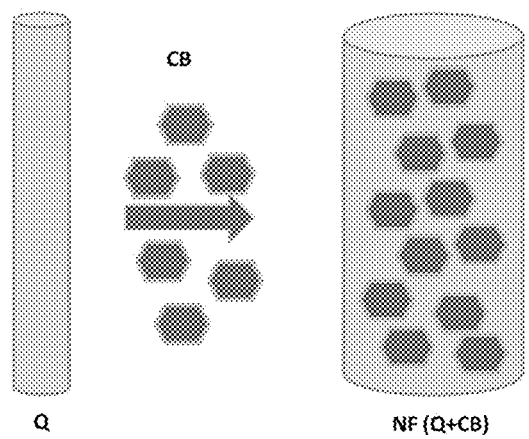
FIG. 1. Diagram of formation of self-assembled nanofibers containing bioactive compounds of the invention. The chitosan polymer (Q) which in the presence of the bioactive compounds (CB) forms the nanofiber of the invention (NF) is observed.

As already anticipated, the invention relates to nanofibers of chitosan and bioactive compounds, where these bioactive compounds are of low molecular size and have acid or lactone groups, aromatic and/or hydroxyl rings. Where the chitosan and the bioactive compounds are structured forming nanofibers through a first interaction of the ionic groups of the molecules and hydrophobic interactions, to be stabilized mainly by the formation of hydrogen bonds between the chitosan and the bioactive compounds, formulating a new system of controlled release of bioactive compounds that are nanocontent in this system. Bioactive compounds that meet these characteristics often have biological activity, especially antioxidant capacity.

The inventors have shown that the nanofibers of the invention are absorbed without degrading in the small intestine and cross the blood-brain barrier, so they are especially useful for delivering neuroprotective bioactive compounds to the brain, such as SLC and, therefore, can be used in the treatment or prevention of neurodegenerative diseases, such as Alzheimer's, Parkinson's, Huntington's, Amyotrophic Lateral Sclerosis (ALS); as well as Ischaemic Strokes and other diseases related to aging or associated with oxidative stress.

The beneficial effect of antioxidants is related to the ability to keep in balance the oxidizing species in an organism, since an increase of them results in Oxidative Stress (EO), associated with cellular and tissue damage and the cause of various pathologies. In particular, the brain is an organ susceptible to EO due to the following phenomena:

a) contains high levels of unsaturated fatty acids, which are vulnerable to oxidation,
b) this organ consumes large amounts of oxygen (around 20% of the total used by the body),
c) the concentrations of endogenous antioxidants are relatively lower in the brain compared to other tissues,
d) the brain contains high concentrations of transition metals like $Cu^+$ and $Fe^{2+}$ which are key catalysts of the damage induced by oxidation (Circu and Aw, 2010, Reactive oxygen species, cellular redox systems, and apoptosis. Free Radic. Biol. Med. 48, 749-762).

The nanofibers of the invention, by allowing the bioactive compounds to be delivered to the brain, would reduce the EO and its associated damages in this very essential organ.

The nanofibers of the invention solve another technical problem. Recently, it has been proven that compounds recognized for their antioxidant action can be pro-oxidants at high concentrations; that is, they have the opposite effect. For this reason, increasing the doses of antioxidants provided in drugs to people can be unsafe and even toxic. The nanofibers of the invention act as a controlled release system, slowly releasing bioactive compounds, such as antioxidants, at concentrations in which their beneficial properties are maintained.

The inventors have found that, surprisingly, by combining chitosan of a molecular size between 70 and 500 KDa and a degree of deacetylation of between 65 to 90%, with bioactive compounds of low molecular size having acidic groups, lactones, aromatic rings or hydroxyls, such as polyphenols of low molecular size, less than 0.5 KDa, spontaneously form the nanofiber of the invention, where the chitosan acts as a nanocontainer for the active compounds protecting them from the intestine to the organs, including the brain. Once in the organs, the nanofiber of the invention degrades slowly, either by changes in acidity or by enzymatic action, releasing the contained active compounds.

It is highly beneficial that the chitosan to be used to obtain the nanofibers of the invention has a less dispersed size, although nanofibers are formed with samples of chitosan of molecular sizes between 70 and 500 KDa, chitosans of smaller molecular sizes are preferred, especially between 80 and 300 KDa, and very especially between 100 and 200 KDa.

Preferably, the chitosan of the invention should have a degree of deacetylation of between 65 to 90%, more preferable between 75 to 85% and especially preferable between 80 to 85%.

In a second aspect, the invention also relates to the method of obtaining the nanofiber, which comprises mixing chitosan of a molecular size between 70 and 500 KDa with the bioactive compounds and allowing self-assembly thereof, as outlined in the FIG. 1. This method comprises mixing a solution of chitosan in concentrations of between 0.5 to 1.5% m/v with a solution of bioactive compounds in concentrations of between 0.1 to 1.5% m/v, where the proportion between both solutions is from 3:1 to 4:1.

The proportion in mass between both components is from 75-85% of chitosan and from 15 to 25% of bioactive compounds.

As indicated, the bioactive compounds useful for the nanofibers of the invention should have a low molecular size, this is a size lower than 0.5 KDa, preferable below 0.4 KDa and especially preferable under 0.3 KDa. Among the compounds that meet the indicated conditions, of having a low molecular size and having acid groups, lactones, aromatic or hydroxyl rings, and which can therefore form the nanofibers of the invention, are gallic acid, quercetin, ellagic acid, ascorbic acid (Vitamin C); hydroxycinnamic acids, such as caffeic, chlorogenic, coumaric, ferulic, sinapic; hydroxybenzoic acids, such as protocatechuic, vanillic, syrinic, rosmarinic; the flavonols kaempferol, myricetin, isoramnetine, among others and their mixtures.

In a preferred embodiment the bioactive compounds correspond to a mixture of the antioxidants gallic acid, ellagic acid and quercetin. In an especially preferred embodiment, the mixture comprises 0.001 to 0.005% m/v ellagic acid, 0.01 to 0.1% m/v quercetin and 0.1 to 1% gallic acid.

The inventors have made various studies with the preferred embodiments of the invention. For example, chitosan nanofibers were developed with a mixture of gallic acid, ellagic acid and quercetin, proving their neuroprotective action both in vitro—in cultures of neurons—and in vivo—in the rat model. In the in vivo model, the results show that the bioavailability of the antioxidants in the brain was enhanced, since by supplying the nanofiber of the invention, a concentration of the antioxidants was obtained more than 7 times higher than that obtained by providing only the antioxidants, see example 3.2. On the other hand, the nanofibers acted as a controlled release system that also increased the stability of the bioactive neuroprotective compounds (antioxidants) against metabolic degradation processes, increasing their activity time in the brain.

Commercially available chitosans may not meet the conditions necessary to form the nanofibers of the invention. For example, we found commercial chitosans of high molecular size (e.g. 575 KDa) and a degree of medium deacetylation (e.g. 67.3%). In this case the chitosan can be subjected to an alkaline treatment to achieve the preferred conditions for carrying out the nanofibers of the invention.

Figure 2:
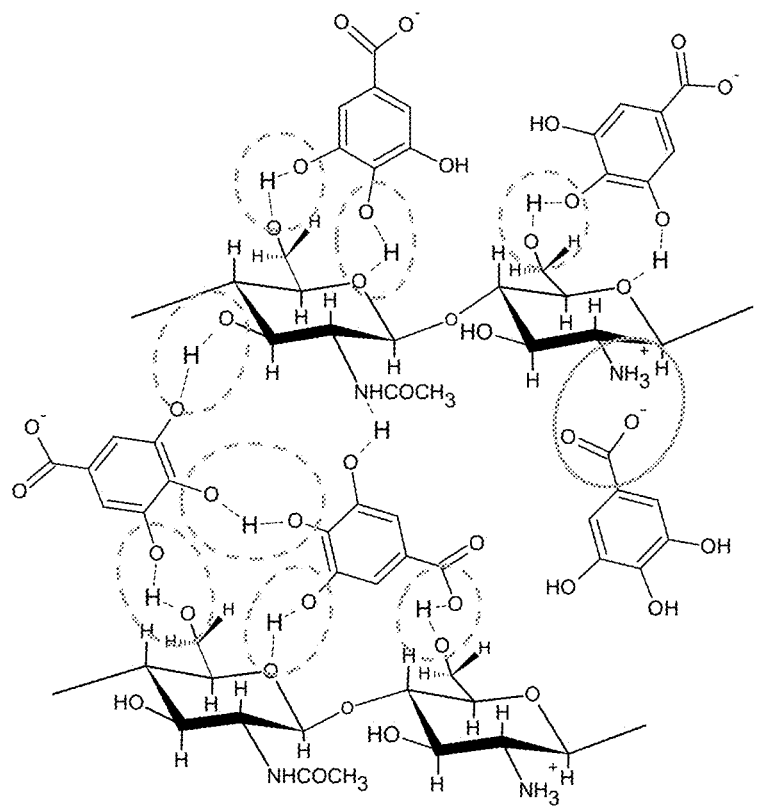
FIG. 2. Representation diagram of interactions present in a chitosan/gallic acid system stabilized by hydrogen bonds in discontinuous circles (- - -) and ionic interactions in continuous circles (—).

Once obtained, chitosan of molecular size between 70 and 500 KDa and a degree of deacetylation between 65 and 90%, it is mixed with the bioactive compounds in the indicated proportions allowing self-assembly of the nanofiber of the invention, which is explained by ionic, hydrophobic and hydrogen bridge interactions between both components of the nanofiber. This was confirmed by Nuclear Magnetic Resonance (NMR) studies of the nanofibers of the invention, which suggest that nanofibers would be stabilized through hydrogen interactions (or bridges). For example, FIG. 2 shows a diagram of the interactions present in a chitosan/gallic acid system where hydrogen bonds are shown in discontinuous circles (- - -) and the ionic interactions are shown in continuous circles (—).

Figure 3:
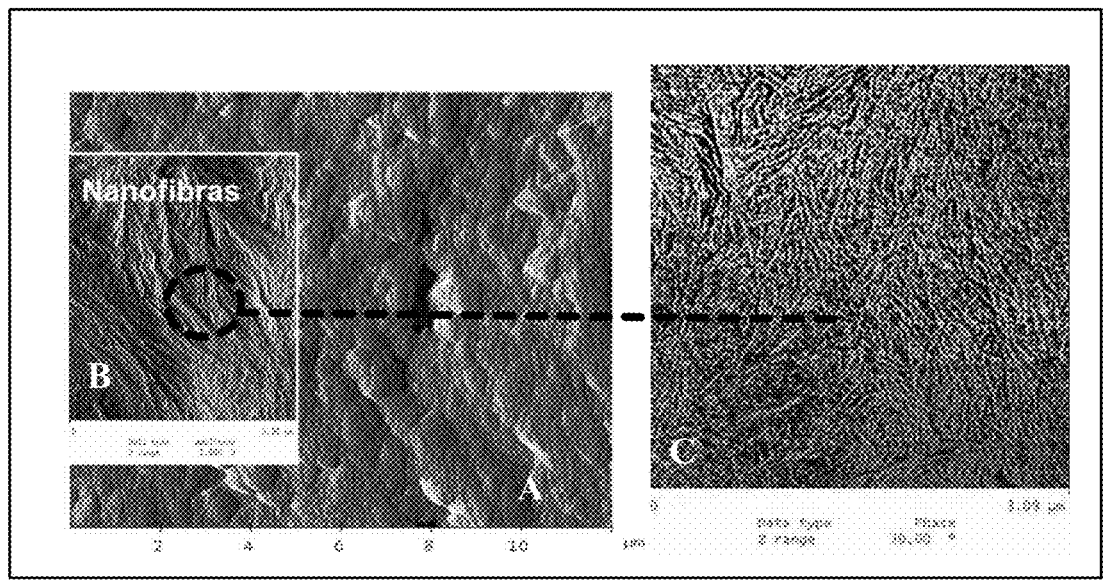
FIG. 3. Atomic Force Microscopy (AFM) images: surface profile of chitosan of average molecular size 120±3.9 KDa and degree of deacetylation between 80 and 85% (A) and antioxidant containing nanofibers of the invention (B—scale μm and C—scale nm).

The presence of the bioactive compounds allows the self-assembly of the chitosan, conforming the nanofiber of the invention. Microscopic studies suggest that bioactive compounds are included in nanofibers. FIG. 3 shows images of Atomic Force Microscopy (AFM) of: chitosan, image (A) under the preferred conditions for the realization of the nanofibers of the invention and of the nanofibers of the invention, after allowing the self-assembly of the chitosan in the presence of bioactive compounds, in this case a mixture of gallic acid, ellagic acid and quercetin; in image B nanofibers are observed on a scale μm and on image C on an nm scale.

Figure 4:
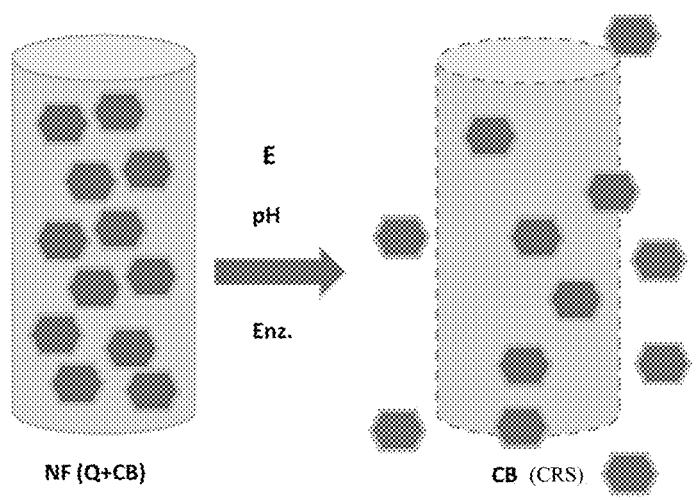
FIG. 4. Functional diagram of the anti-oxidant containing nanofibers of the invention, such as controlled release systems (SLC), the nanofiber of the invention (NF), before chemical stimuli (E) such as changes in acidity (pH), or biological enzymes (Enz.) Release the bioactive compounds (CB) to the medium.
Figure 5:
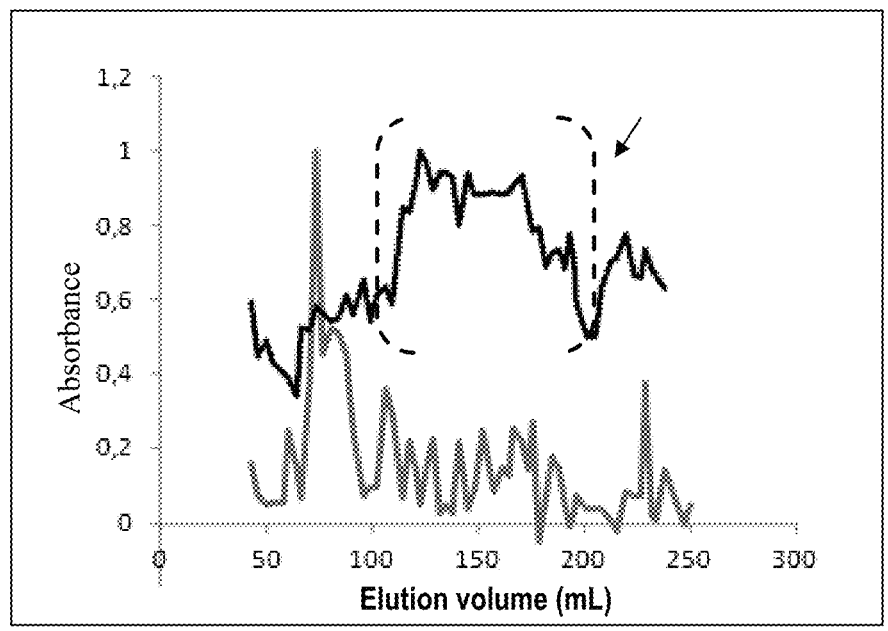
FIG. 5. Elution curve of chitosan treated according to example 1.2, where chitosan, (black line) and commercial chitosan (gray line) are depolymerized and deacetylated in Sepharose 4B-CL. The arrow indicates the fraction of chitosan treated with lower polydispersity.

The inventors carried out a complete study of antioxidant containing nanofibers as a controlled release system (SLC), which was performed through Nuclear Magnetic Resonance (NMR), subjecting the systems to pH stimuli, increasing the acidity, finding that in environments strongly acidic bioactive compounds and chitosan behave independently (absence of interactions) demonstrating their functioning as release systems responding to chemical stimuli (changes in acidity) which is outlined in FIG. 4. In addition, the existence must be considered of biological components, such as the presence of enzymes in the brain or other organs capable of degrading chitosan, which would allow the controlled release of bioactive compounds in vivo.

According to the above, the nanofibers containing bioactive compounds, such as antioxidants, based on chitosan of the invention have a greater bioavailability of the antioxidants in the brain and will release the latter in function of the stimuli that diminish the interactions that are present in the brain. form among them, conditioning their release rate and generating controlled release systems that increase the safety and innocuousness in their potential use as a neuroprotector and/or neuroregenerator at the brain level.

Obviously, the nanofibers of the invention can be used to deliver bioactive compounds to the whole organism, in the different organs. However, since one of the advantages of the invention is that it allows passage through the BBB, the examples are focused on the brain. In this organ, the nanofibers of the invention can be used, when supplied as a pharmaceutical or nutraceutical composition, to prevent or treat neurodegenerative diseases, such as Alzheimer's, Parkinson's, Huntington's, Amyotrophic Lateral Sclerosis (ALS) and related. As well as to prevent or treat Ischaemic Strokes.

The nanofibers of the invention can be incorporated in a pharmaceutical or nutraceutical composition, together with formulation excipients and optionally in combination with other active ingredients. Given the characteristics of the nanofibers of the invention, which are absorbed at the level of the small intestine without being degraded, convenient pharmaceutical compositions suitable for oral administration can be formulated, such as tablets, coated tablets, powders, capsules, syrups or others. However, this is not limiting and it is understood that the nanofibers of the invention can be formulated in any type of pharmaceutical form existing in the state of the art. Additionally, the nanofibers of the invention can be mixed with food or beverages. Obviously, pharmaceutical or nutraceutical compositions can be administered to both humans and animals, as required.

As indicated and demonstrated in the examples, in the objective organs, the nanofibers of the invention act as a controlled release system of the bioactive compounds it contains, at the beginning of the disassembly of the nanofiber and/or the biodegradation of the chitosan.

The invention can be better understood in the light of the examples included below, which are merely illustrative of preferred embodiments of the invention and should not be considered as limitations thereof.

EXAMPLES

1. Preparation of Nanofibers of the Invention

1.1 Preparation of the Mixture of Bioactive Compounds to Nano-Contain.

A solution of 25 mg of ellagic acid, 45 mg of quercetin and 700 mg of gallic acid was prepared for 100 mL of a 75% v/v aqueous ethanol solution. It was stirred at room temperature until complete dissolution of the compounds.

The structure of these compounds is shown below:

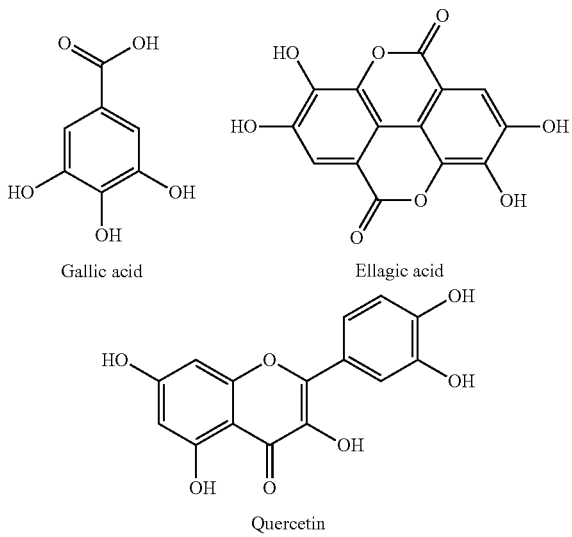

Gallic acid    Ellagic acid

Quercetin

1.2 Procedure for Obtaining Nanofibers of Chitosan and Antioxidants

The mixture to form nanofibers was made by pouring 75 mL of an aqueous solution of chitosan with a molecular size of 121±3.9 KDa and a degree of deacetylation of 85%, at 1% m/v on 25 mL of the solution obtained in the point 1.1. It was stirred vigorously and stored at 4° C.

Under these conditions, polyphenols interact with chitosan through ionic interactions (carboxyl group of antioxidants and amino group of polysaccharide) changing its three-dimensional structure to favor the hydrophobic interactions between the aromatic rings of polyphenols and the hydrocarbon chain of glucosamine, the nanofibers of the invention are spontaneously formed and finally stabilized by hydrogen bonds.

1.3 Morphological Characterization of the Nanofibers Obtained in the Previous Point Through Atomic Force Microscopy (AFM)

1.3.1 Development of Membranes for Solid Phase Studies

To obtain membranes from the suspension of nanofibers obtained in the previous point (1.2), 6 mL of the solution was spread in a Petri dish of 10 cm in diameter. This volume is sufficient to cover the smooth surface of the polycarbonate plate. Then it was dried in a culture oven at 50° C. for 6 h.

1.3.2 Characterization of Nanofiber Membranes by AFM

The resulting membranes in the previous point were analyzed by Atomic Force Microscopy (AFM) for their morphological characterization. This technique provided three-dimensional images that allowed to quantify the depth and morphology of the samples, corroborating the formation of nanofibers (FIG. 3). FIG. 3 A shows the surface profile of the chitosan able to form nanofibers of the invention, in this case it is of a molecular size of 121±3.9 KDa. FIGS. 3 B and 3 C show the nanofibers of the invention obtained in Example 1.1, where the image 3 B is on a μm scale and the image 3 C is on a nm scale.

2. Neuroprotection Effect of the Nanofibers of the Invention In Vitro on Rat Hippocampal Neurons

2.1 Primary Rat Hippocampal Culture:

Brains were used from 18-day rat embryos. The extracted hippocampi were placed in modified Hanks saline solution (mHBSS, for its name in English: Hank's buffer salt solution) and washed three times to then add trypsin (0.25%). After this treatment, the hippocampi were washed with mHBSS and transferred to a MEM medium (Minimum Essential Medium) supplemented with 10% horse serum (HS), disintegrating with Pasteur pipette. The cell suspension was collected by low speed centrifugation (2000×g× 20 s) at room temperature. The supernatant was saved and the pellet was broken up again with a very fine tip Pasteur pipette. Another centrifugation was performed at low speed (2000×g×20 s) at room temperature. The supernatant containing the cells in suspension was pooled with the above supernatant and the viable cells were counted using Trypan blue (0.2%). Subsequently, the neurons were seeded in culture plates in MEM supplemented with 10% HS. After the hippocampal neurons adhered to the plaque, they were exchanged for medium with a Neurobasal medium with the culture supplement B27, remaining in culture for fourteen days.

2.2 In Vitro Studies in Rat Hippocampal Neurons.

The hippocampal neurons of rat obtained in point 2.1 were used to evaluate the neuroprotective effect of the nanofibers of the invention.

Initially, the percentage of cellular viability of said hippocampal neurons exposed to different concentrations of hydrogen peroxide was evaluated. (10, 50, 100, 200, 500 μM) during 1 h. Hydrogen peroxide ($H_2O_2$) under biological conditions, it is a highly oxidizing compound.

Figure 6:
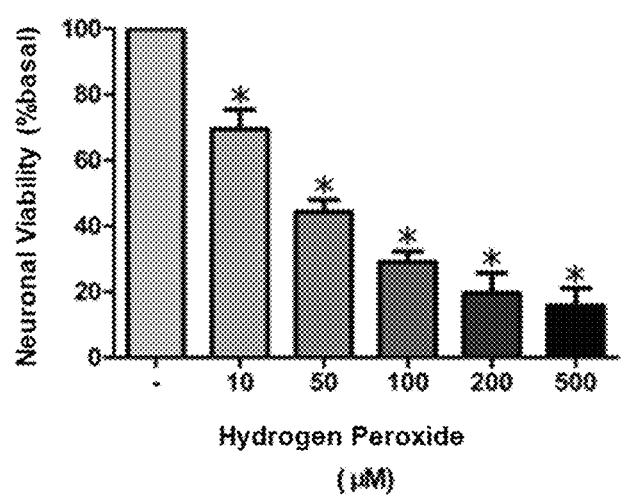
FIG. 6. Hippocampal neurons cell viability 24 hours after exposure to different concentrations of hydrogen peroxide (10, 50, 100, 200, 500 μM) for 1 h. * Statistical significance with respect to the control without peroxide treatment ($p<0.05$).

In all conditions used changes in cell viability were observed with respect to the control condition without $H_2O_2$, the percentages of viability with respect to the baseline condition were 69,45±6; 44,33±4; 29,06±3; 19,59±6 and 15,81±5 respectively, for the aforementioned concentrations of $H_2O_2$. At all concentrations, the decrease in viability was significant with respect to the control condition (p<0.05, n=4). These results are shown in FIG. 6.

For the subsequent tests it was decided to use a hydrogen peroxide concentration of 50 μM for one hour since neuronal viability decreases by about 50% in this condition, 24 hours after incubation with $H_2O_2$.

2.2.1 Protective Effect of a Mixture of Antioxidants Against Oxidative Damage by $H_2O_2$.

The neuroprotective effect of the antioxidant mixture (AOX) was evaluated, for which the neurons obtained in point 2.1 were incubated for 24 hours in a medium supplemented with the mixture of antioxidants obtained in Example 1.1. Neuronal viability was compared to control (incubated with the vehicle without antioxidants) at concentrations of 0.001, 1, 10, 100, 150 and 200 μM of AOX, before and after the exposure of crops to a concentration of 50 μM of $H_2O_2$, during 1 h of incubation.

Figure 7:
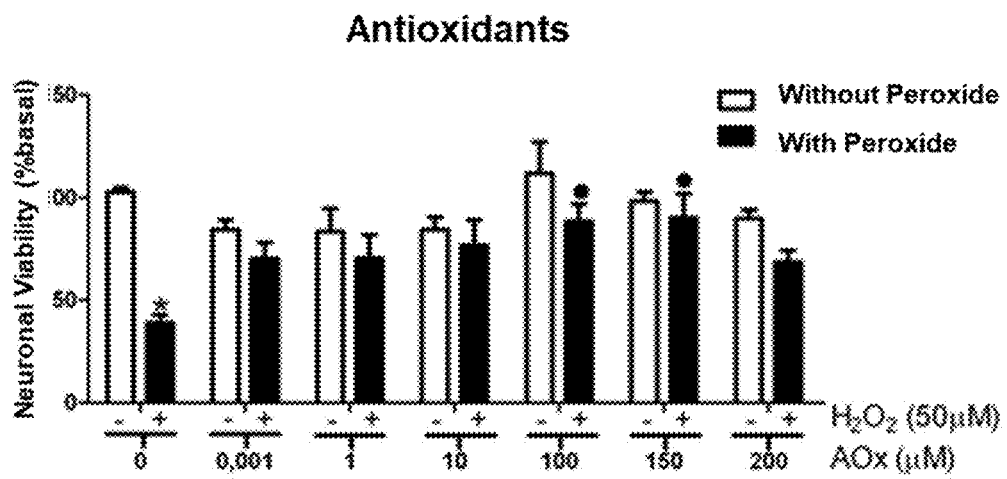
FIG. 7. Neuronal viability of hippocampal cultures, pre-incubated 24 hours with the vehicle or with AOX at concentrations of 0.001, 1, 10, 100, 150 and 200 μM, determined 24 h after the exposure of the cultures to 50 μM of hydrogen peroxide for 1 h. * Statistical significance with respect to the control without peroxide treatment ($p<0.05$). Statistical significance with respect to the group treated with peroxide ($p<0.05$).

The results are shown in FIG. 7, where it can be seen that:
in the control condition the $H_2O_2$ decreases cell viability to less than 50%;

in all concentrations of AOX, without $H_2O_2$, it was not possible to show significant differences with respect to the control;

the protective effect of AOX is statistically significant only at concentrations of 100 and 150 µM.

2.2.2 Protective Effect of the Nanofibers of the Invention Against Oxidative Damage by $H_2O_2$.

The neuroprotective effect of the nanofibers of the invention (NF) was evaluated, for which the neurons obtained in point 2.1 were incubated for 24 hours in a medium supplemented with the nanofibers of the invention obtained in Example 1.2. The neuronal viability compared to the control (incubated with the vehicle without nanofibers) was compared with nanofibers containing concentrations of 0.001, 1, 10, 100, 150 and 200 µM of AOX, before and after the exposure of crops to a concentration of 50 µM of $H_2O_2$, during 1 hour of incubation.

Figure 8:
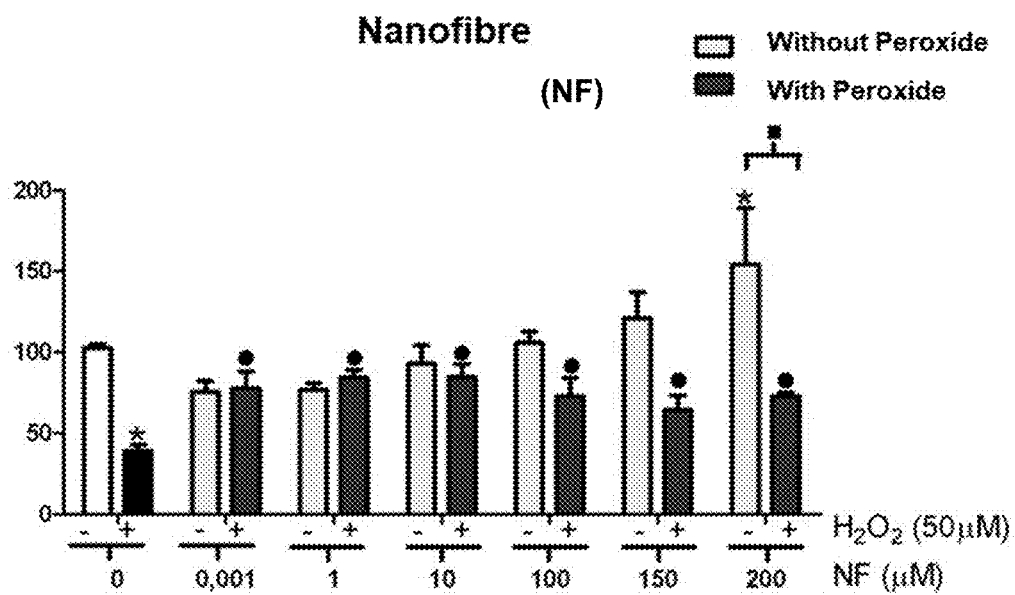
FIG. 8. Neuronal viability of hippocampal cultures, pre-incubated 24 hours with the vehicle or with NF, where the concentrations associated with NF refer to the content of AOX in the nanofibers of the invention, at concentrations of 0.001, 1, 10, 100, 150 and 200 μM determined 24 h after the exposure of the cultures to 50 μM of $H_2O_2$ for 1 h. * Statistical significance with respect to the control without peroxide treatment ($p<0.05$). Statistical significance with respect to the group treated with peroxide ($p<0.05$). Statistical significance between the groups treated with NF, with and without peroxide.

The results are shown in FIG. 8, where as indicated the NF concentrations refer to the AOX content in the nanofibers of the invention; it is appreciated that:

in the control condition the $H_2O_2$ decreases cell viability to less than 50%;

In absence of $H_2O_2$ a decrease in cell viability is observed in cultures with low concentrations of NF (0.001, 1 and 10 however, said decrease is not statistically significant;

in the concentration of 200 µM of NF, without $H_2O_2$, there is a significant increase in neuronal viability compared to the control;

in all concentrations of nanofiber, in front of the injury by hydrogen peroxide showed significant increases in neuronal viability ($p<0.05$) with respect to the control with 50 µM of $H_2O_2$.

These results demonstrate that the nanofibers of the invention provide better protection against oxidative stress than free antioxidants, that is, not contained in nanofibers in in vitro cultures.

3. Determination of the Bioavailability of Antioxidants in Extracts of Animal Brains 3.1 In Vivo Studies of Bioavailability In vivo bioavailability studies were carried out on female rats Sprague dawley (n=9), of 350 g of average mass approximately, of 14 months of age.

The animals had a period of 14 days of administration of 200 µL of suspension of nanofibers containing an antioxidant mixture with a total concentration of 3.9 mg/mL (gallic acid, ellagic acid and quercetin) for the group treated with the nanofiber of the invention (NF), a solution of the acid polyphenols Gallic acid, ellagic acid and quercetin in the same total concentration of 3.9 mg/mL for the antioxidant control group (AOX).

All rats were maintained in an environment between 23-24° C. and a relative humidity of 50%, water and normal pellet feeding ad libitum, subjecting to circadian cycles of 12:12 hours/light: dark. No noticeable morphological changes or erratic behaviors were observed.

3.2 Bioavailability Study

At the end of the antioxidant supply period (AOX) or the nanofibers of the invention (NF), 18 hours are expected to obtain the brains and extract the antioxidants for their subsequent identification and quantification. The determination of the amount of antioxidants in rat brain tissues was performed, after perfusion (sucrose 110 mM, NaCl 60 mM, KCl 3 mM, $NaH_2PO_4$ 1.25 mM, $NaHCO_3$ 28 mM, D-glucose 5 mM, $CaCl_2$ 0.5 mM, $MgCl_2$ 7 mM and 95% $O_2$/5% $CO_2$), to move indications of blood in the brain and lower brain temperature.

Then the brain samples were frozen and pulverized in a ceramic mortar previously cooled with liquid nitrogen. The pulverized tissues were extracted with 10 mL of precooled methanol at −20° C. and the brain homogenates were centrifuged at 7500×g for 20 minutes. The supernatant was subjected to drying through a stream of nitrogen ($N_2(g)$). The samples were reconstituted with 2 mL of ultra pure distilled water (previously filtered in membranes of 0.22 µm) and fractionated through a preparative C-18 reverse phase column (Sep-Pak-Waters silica columns). Then, the antioxidants were separated into neutral and acid, according to the methodology described by Kim and Lee (2002, Extraction and Isolation of Polyphenolics, Current Protocols in Food Analytical. Unit I-1.2).

The fractions obtained (neutral antioxidants and acid antioxidants) were reconstituted with 5 mL of methanol, to be analyzed by high performance liquid chromatography (HPLC for its acronym in English) in a chromatograph coupled to a detector with diode array (HPLC-DAD), with the following conditions: injection volume 50 µL, temperature 30° C., detector wavelength 272 nm for gallic acid and 376 nm for quercetin, mobile phase in ascending polarity: solvent A: acetic acid at 1% v/v and solvent B: methanol and HPLC column Inertsil ODS-3 C 4.6 ID×150 mm (5 µm).

A linear relationship is established between the amount of antioxidant and its response area by liquid chromatography. For gallic acid measurements were made at the maximum absorption (272 nm) of this compound, finding a linear response between 11.2-112.0 µg/mL, with a linear correlation coefficient of 0.9993, which indicates that the spectrum corresponds to this compound.

Figure 9:
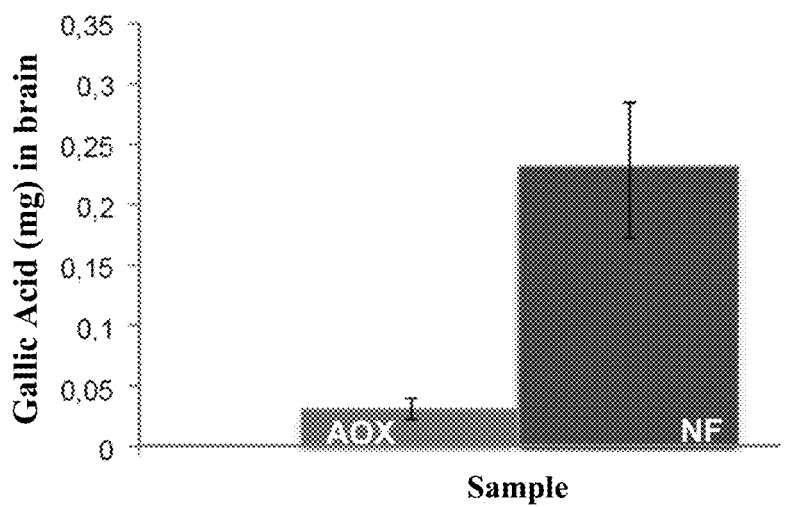
FIG. 9. Comparison chart of bioavailable gallic acid in brain after 14 days of supply of the same concentration of AOX, the first bar corresponds to animals with only the AOX mixture (light gray, AOX) and the second bar corresponds to animals with antioxidant supply contained in the nanofibers of the invention (dark gray, NF).

Gallic acid was used as a marker of bioavailability in the brain, since of the 3 compounds used it is the one that can be extracted more efficiently and is normally used for this purpose. Therefore, the evaluation of bioavailability is carried out in relation to the brain content of gallic acid, which is 7.6 times higher in the mice treated with the nanofibers of the invention in relation to the animals treated with antioxidant control (AOX). The results are presented in FIG. 9. The analysis of ANOVA shows that the difference found between the groups treated only with antioxidants (AOX) and with nanofibers (NF) is significant with $p<0.05$ ($p=0.038$).

This analysis demonstrates that the nanofibers of the invention significantly increase the bioavailability of the antioxidants in the brain when administered orally, with respect to the supply of the same amount of free antioxidants, not contained in the nanofibers.

3.3 In Vivo Studies of Cerebral Neuroprotection

Brain neuroprotection studies in vivo were carried out in male rats Sprague dawley (n=11), of 350 g of average mass approximately each one, of 18 months of age.

The 18-month-old or aged animals had a period of 50 days of administration of 200 µL of suspension of nanofibers containing a mixture of antioxidants with a total concentration of 3.9 mg/mL (gallic acid, ellagic acid and quercetin) for the group treated with the nanofiber of the invention, 200 µL of suspension of a mixture of antioxidants with a total concentration of 3.9 mg/mL (gallic acid, ellagic acid and quercetin) for the group treated only with the antioxidants of the invention, while the control group received a standard diet.

All rats were maintained in an environment between 23-24° C. and a relative humidity of 50%, water and normal pellet feeding ad libitum, subjecting to circadian cycles of 12:12 hours/light: dark. No noticeable morphological changes or erratic behaviors were observed in any of the groups.

3.3.1 Preparation of Hippocampal Slices:

The hippocampi of male Sprague dawley rats aged 18 months with and without administration of nanofibers of the invention and only with the mixture of antioxidants present in the nanofibers (same antioxidants and their concentration), were extracted and quickly placed in a saline solution. Cutting containing: sucrose_110 mM, NaCl 60 mM, KCl 3 mM, $NaH_2PO_4$ 1.25 mM, $NaHCO_3$ 28 mM, D-glucose 5 mM, $CaCl_2$ 0.5 mM, $MgCl_2$ 7 mM, ascorbic acid 0.6 mM and 95% $O_2$/5% $CO_2$ balancing the solution. A vibratome was used to cut slices of 400 µm, which were transferred to a 1:1 mixture of cutting solution and artificial cerebrospinal fluid (ACSF) composed of: NaCl 125 mM, KCl 2.5 mM, $NaH_2PO_4$ 1.25 mM, $NaHCO_3$ 25 mM, D-glucose 25 mM, $CaCl_2$ 2 mM and $MgCl_2$ 1 mM, also balanced with 95% 02 and 5% $CO_2$. The slices were kept at room temperature for at least thirty minutes and then, they were transferred to a recording chamber where they were stabilized and perfused only with ACSF at 32° C. for one hour before conducting the electrophysiological experiments.

Figure 10:
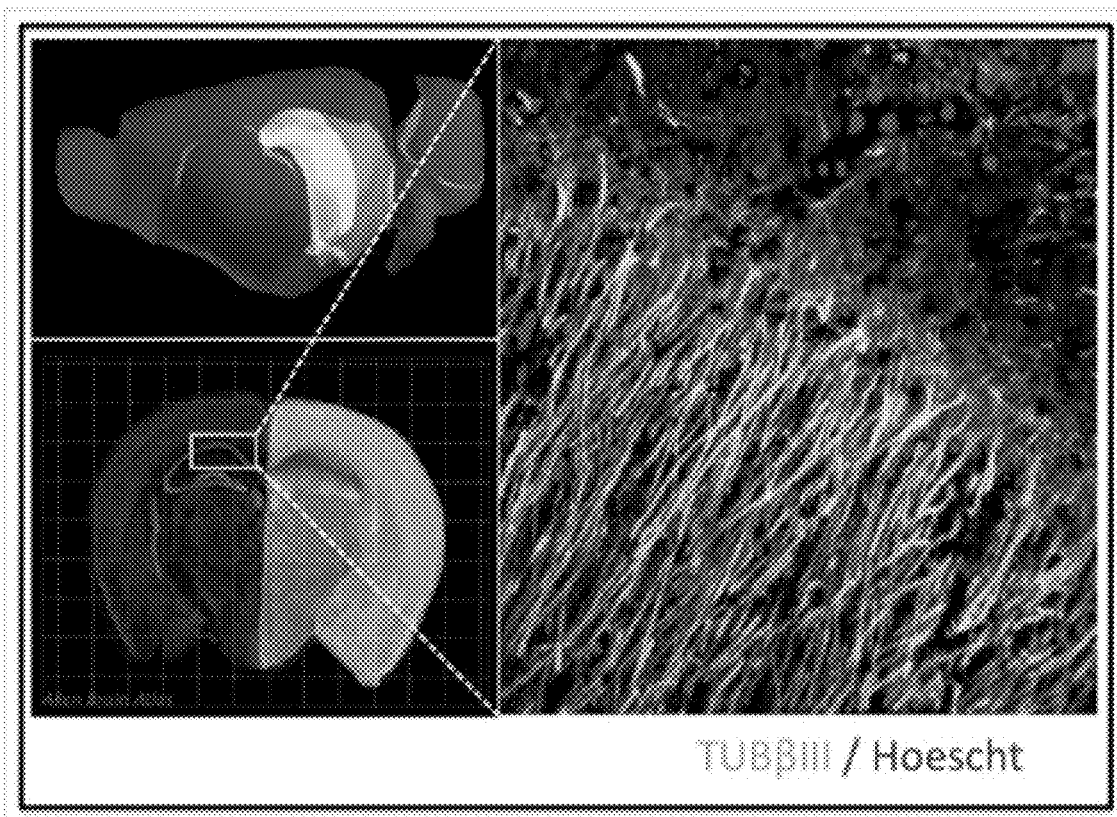
FIG. 10. CA1 zone of the hippocampus evaluated in the examples.

3.3.2 Electrophysiological Recordings in Hippocampal Slices:

To obtain the electrophysiological data, four slices of hippocampus were stimulated simultaneously, using two independent recording chambers, with two slices per chamber. The synaptic responses were evoked by stimulating the Schaffer collateral fibers with 0.2 ms pulses applied with a concentric bipolar stimulation electrode and recorded extracellularly in the stratum radiatum of the CA1 area of the hippocampus, which is shown in FIG. 10. basal response was obtained by stimulation every 30 seconds for 20 minutes, using a current intensity that evokes a slope of the field potential (fEPSP) equivalent to half the maximum slope, until the application of an electrical stimulation protocol that induces a long-term potentiation (LTP for its acronym in English, Long-term potentiation) in the synaptic response. The applied protocol consists of a high-frequency tetanic stimulation train (TBS: Theta Burst Stimulation) consisting of ten tetanus (bursts) separated by 200 ms (5 Hz). Each tetanus composed of four pulses separated by 10 ms each (100 Hz). The induction of LTP was performed with an induction protocol consisting of four trains of high frequency tetanic stimulation (4×TBS) applied every 20 s (0.05 Hz).

The LTP, since its discovery has been proposed as a cellular model of the processes that underlie learning and memory. Two fundamental analogies support the suggestion that LTP could be considered a good model of learning and memory: the fact that long-term empowerment is a change of lasting connectivity that depends on activity and that was described in the hippocampus, a related structure with memory.

Figure 11:
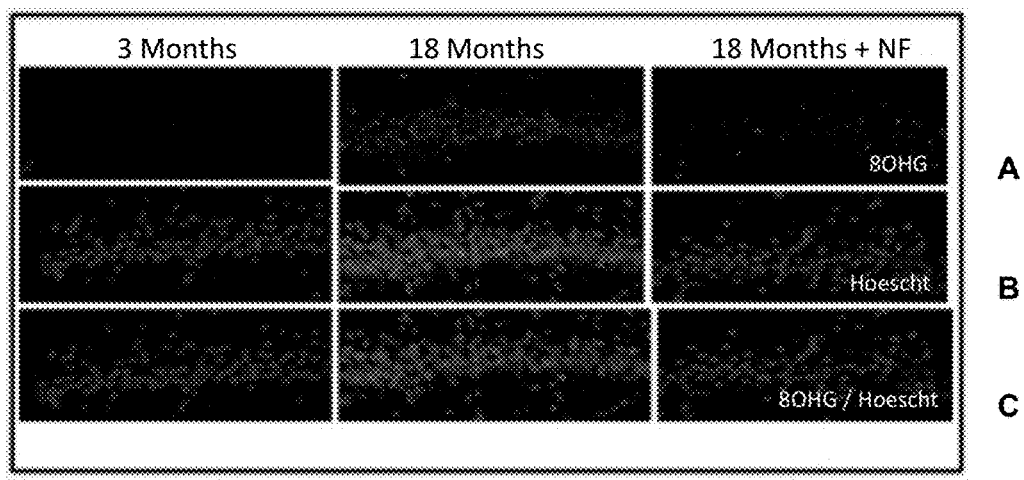
FIG. 11. Hippocampal slices (zone CA1) marked with an antibody that detects oxidation of DNA (anti-8-hydroxyguanosine, 8-OHG) (row A) and counterstaining of the nucleus (Hoechst) (row C) and both (row B) in young animals of 3 months, aged 18 months and aged 18 months with diet supplemented with nanofiber for 50 days.

3.3.3 Records of DNA Oxidation in Hippocampal Slices:

The hippocampal slices obtained in 3.3.1 were incubated with an antibody that detects oxidation of DNA, fluorescently marked in red. The results are shown in FIG. 11. In the upper row (A) the immunofluorescence of DNA oxidation is shown using an anti-8-hydroxyguanosine antibody (8-OHG), which detects oxidation of DNA, in the lower row (C) the neuronal nucleus is stained in blue (Hoeschst contratinction), and in the center is shown the counter-staining of the nucleus and the immunofluorescence of DNA oxidation (B). It can be clearly observed that in the analyzed region, the oxidative damage associated with DNA in old animals (18 months, A) is significantly higher than in young animals (3 months, A), and that old animals fed a diet supplemented with Nanofibers of the invention (18 months+NF, A), significantly decrease the oxidative damage in their DNA.

3.3.4 Effect of Nanofiber on Synaptic Plasticity in Aged Rats

For this study, LTP induced by tetanic stimulation was evaluated in hippocampal slices of rats aged in three feeding conditions for 50 days: standard diet or control (CT), food supplemented with 200 µL of a mixture of antioxidants with a total concentration of 3.9 mg/mL (gallic acid, ellagic acid and quercetin) (AOX) and food supplemented with 200 µL of suspension of nanofibers of the invention containing a mixture of antioxidants with a total concentration of 3.9 mg/mL (gallic acid, ellagic acid and quercetin) (NF).

Figure 12:
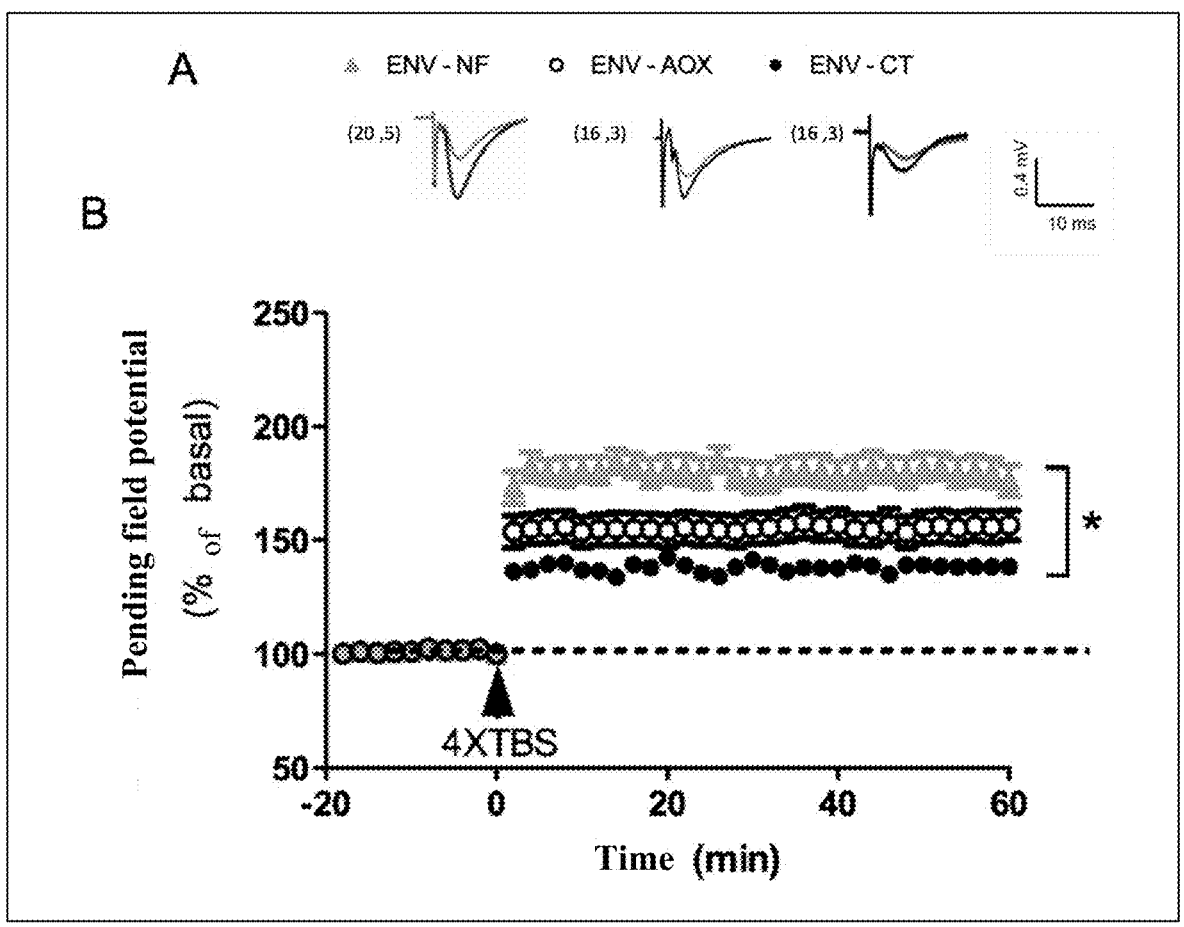
FIG. 12. Synaptic plasticity induced by tetanic stimulation in hippocampal slices of rats aged in three feeding conditions for 50 days: standard diet or control (CT), diet supplemented with 200 µL of a mixture of antioxidants with a total concentration of 3.9 mg/mL (gallic acid, ellagic acid and quercetin) (AOX) and food supplemented with 200 µL of suspension of nanofibers of the invention containing a mixture of antioxidants with a total concentration of 3.9 mg/mL (gallic acid, ellagic acid and quercetin) (NF). A) Traces representatives of the field potentials evoked in each condition. The values in parentheses indicate the number of slices and the number of animals used. B) Effect of nanofiber on the LTP in neurons of the CA1 area, induced by trains of high frequency stimulation (TB S) in CA3 afferent fibers (collaterals of Shaffer) in the hippocampus of aged rats. The results are presented as average±standard error. * indicates significant difference with respect to control. Statistics p<0.05 evaluated with the student test.

The results are shown in FIG. 12, where it can be seen that the LTP induced by tetanic stimulation in hippocampal slices of rats aged with the diet supplemented with antioxidants (ENV-AOX) obtained better results than the control rats (ENV-CT), however, this difference is not significant. On the contrary, the results on rats fed with nanofibers (ENV-NF) are even better, in this case the difference is statistically significant with respect to the control.

Again the results demonstrate that in vivo the effect of the antioxidants supplied orally in the nanofibers of the invention is substantially better than that of the free antioxidants or those not contained in the nanofibers.

4 Study of Interactions of the Nanofibers of the Invention by NMR

To assess that the interactions between chitosan and the active compounds are, as has been proposed, hydrogen bond interactions, and that therefore the nanofibers of the invention act as controlled release systems in vivo, spectroscopic resonance studies were performed. Nuclear magnetic (NMR) comparing the antioxidants (AO) ascorbic acid and free gallic acid and in the nanofiber of the invention, as well as the isolated chitosan.

4.1 NMR of Isolated Antioxidants.

Figure 13:
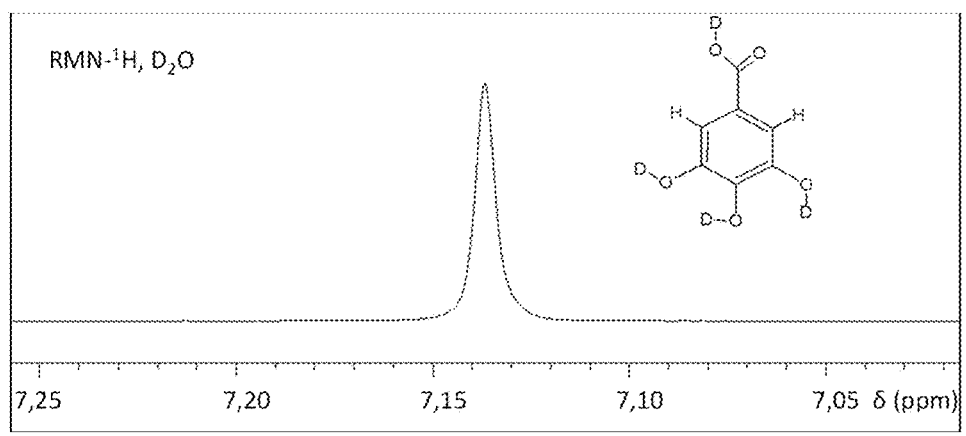
FIG. 13. NMR spectrum $^1$H of gallic acid, in $D_2O$, at pD 3 and 37° C.
Figure 14:
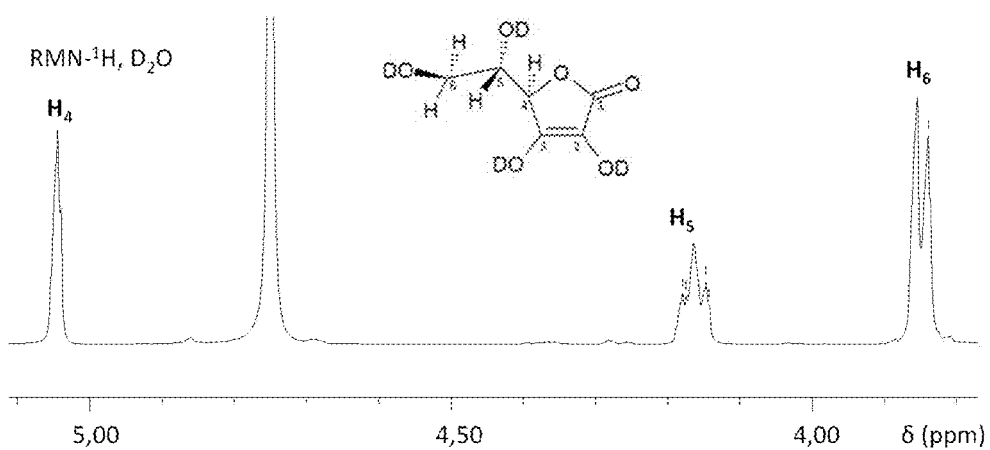
FIG. 14. NMR spectrum $^1$H of ascorbic acid, in $D_2O$, at pD 3 and 37° C.

The NMR spectroscopic studies are performed for the antioxidants ascorbic acid and free gallic acid. First, gallic acid was chosen as the AO, whose molecule has a single hydrogen atom, which corresponds to 2 equivalent positions with respect to the carboxylic group, which are the only hydrogen atoms in the formula of FIG. 13, the hydrogens of the hydroxyl groups are silenced by isotopic exchange with deuterated water -$D_2O$. The second AO studied was the ascorbic acid or Vitamin C which was chosen for being a recognized antioxidant and because conveniently for an NMR study it has 3 hydrogen atoms that can be studied, one in the ring in the position $C_4$ and two out of the ring in the positions $C_5$ and $C_6$. These positions and the NMR spectrum $^1H$ of ascorbic acid, are shown in FIG. 14.

4.2 NMR of Antioxidants in the Nanofiber of the Invention.

For this study, nanofibers of the invention were formed with both antioxidants separately. 750 µL of chitosan with a molecular size of 121±3.9 KDa and a degree of deacetylation of 85% at a concentration of 30 mg/mL over 250 µL of gallic acid or ascorbic acid at a concentration of 5 mg/mL are mixed. It is agitated vigorously and the spontaneous formation of the nanofibers of the invention is allowed.

Both nanofibers are subjected to analysis by NMR spectroscopy after an isotopic exchange with $D_2O$ (deuterated water), by varying the pH/pD between 5 and 1 with HCl/DCl (deuterated hydrochloric acid) at 37° C., the water signal is used as reference (δ 4.75 ppm). In both cases studied, when recording the spectrum for the antioxidants in the nanofibers of the invention (NF)-AO at neutral pH, the clear signals for the AO were not observed, which implies that the AO molecules were not free in the solution, by increasing the acidity to pD/pH 3 and then to pD/pH 1 the characteristic signals of the AO protons were appearing, to then present displacements similar to those observed in the absence of chitosan of the invention. The behavior of the chitosan-AO systems when forming the nanofibers of the invention proves the existence of interactions between both by hydrogen bonds, since these interactions are modified by changing the acidity of the solution.

4.2.1 NMR of Gallic Acid in the Nanofiber of the Invention

Figure 15:
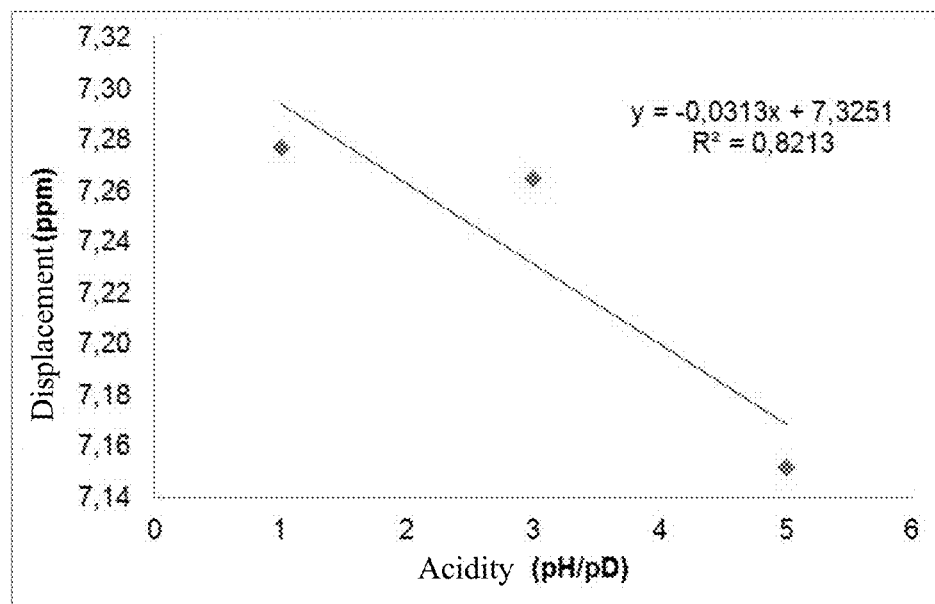
FIG. 15. Graph of relationship between the displacements (ppm) of the gallic acid signal in the chitosan-gallic system and the acidity of the medium.

Displacement of signals of NMR spectra $^1$H accounts for interactions between the two components of the system (chitosan-gallic acid). FIG. 15 allows to relate the displacement of system signals associated with gallic acid to the different pH studied, where a linear behavior is observed ($R^2$=0.8213) by decreasing the acidity of the system (Table 1), giving an account of the existence of interactions between the antioxidant and chitosan.

TABLE 1

Assignment of the gallic acid signal in the chitosan-gallic system.

| Acidity pH/pD | H/ppm NF | Reference |
|---|---|---|
| 1 | 7.28 | 7.14 |
| 3 | 7.27 | |
| 5 | 7.15 | |

In the system of the nanofiber of the invention conformed by chitosan and gallic acid to pD/pH 1, the acid is under its $PK_a$ (4.4), so the carboxylate group is predominantly protonated (—COOH), decreasing the possibility of ionic or electrostatic interactions, but favoring hydrophobic and hydrogen bonding interactions, the latter being the ones that would explain the most important interaction between the two. The structure of gallic acid at pH 4.4 is shown below:

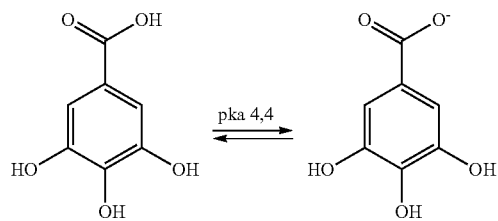 [SMILES: O=C(O)c1cc(O)c(O)c(O)c1 ; O=C([O-])c1cc(O)c(O)c(O)c1]

Figure 16:
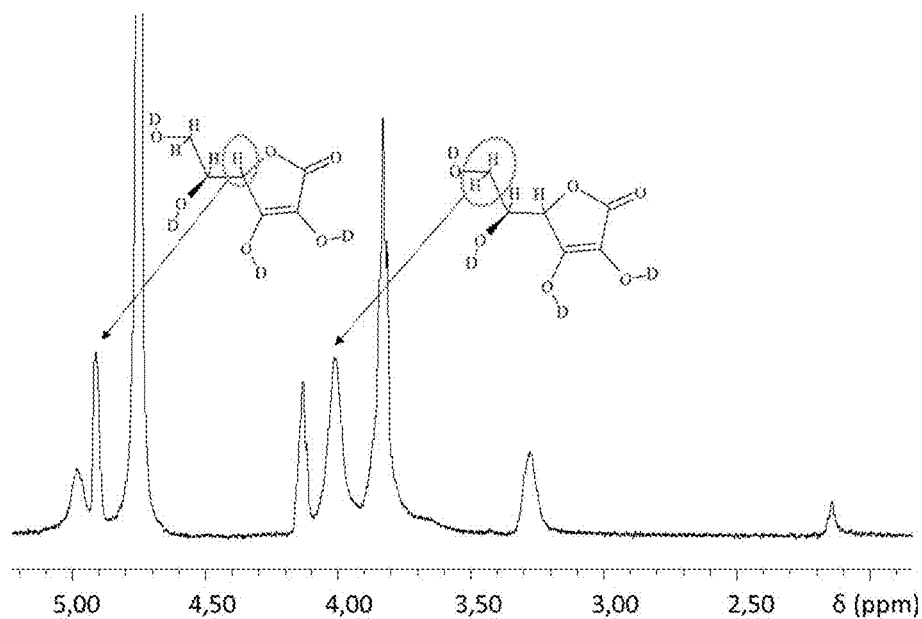
FIG. 16. NMR spectrum $^1$H of the chitosan-ascorbic acid system, in $D_2O$, at pD 5, and 37° C.

Acid-base equilibrium of gallic acid in aqueous media 4.2.2 NMR of Ascorbic Acid in the Nanofiber of the Invention On the other hand, for the ascorbic acid, the NMR spectrum was recorded $^1$H a pD/pH 5, shown in FIG. 16. At said acidity a deformation was observed in the signals of the chitosan-ascorbic acid nanofibers, where the proton of the $C_4$ of ascorbic acid shows a high field displacement (4.91 ppm) showing the presence of an ionic interaction of ascorbate with the protonated amino group of the glucosamine unit of chitosan, since the system is at values above its pKa (4.2). The structure of ascorbic acid at pH 4.2, is shown below:

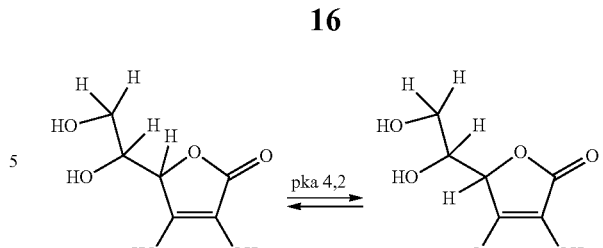

Acid-base balance of ascorbic acid in aqueous media.

Table 2 shows the chemical shifts of ascorbic acid signals in the NMR spectrum $^1$H of the chitosan-ascorbic acid system at 37° C. in $D_2O$ and at different pD/pH.

TABLE 2

Assignment of the displacements of ascorbic acid signals in the chitosan-ascorbic acid system.

| Assignment | Displacement/ppm of Ascorbic Acid | | |
|---|---|---|---|
| Proton | pD/pH 1 | pD/pH 3 | pD/pH 5 |
| $H_4$ of $C_4$ | 5.072-5.065 | 5.056-5.045 | 5.045-5.095 |
| $H_5$ of $C_5$ | 4.190-4.154 | 4.188-4.152 | 4.143-4.174 |
| $H_6$ of $C_6$ | 3.853-3.845 | 4.862-3.844 | 3.840-3.855 |

The displacements of the signals of the hydrogen nuclei of the ascorbic acid to the different degrees of acidity (FIG. 17), showed a direct relationship between the acidity of the medium in which the nanofiber is located and the low field displacement of the hydrogen nucleus of $C_4$, corroborating the interaction between ascorbic acid and chitosan in the systems studied.

The analysis of the proton displacement of $C_4$ of the ascorbic acid lactone ring at low field confirms that the most important interactions would occur through hydrogen bonds of the hydroxyl groups and carbonyls of the acid lactone ring with the hydroxyl groups of the chitosan, since this proton is part of the ring of the lactone.

Therefore, the most important effect of the increase in acidity was observed in the hydrogen nucleus of the $C_4$, showing an interaction of the antioxidant with chitosan by the formation of hydrogen bonds, and to a lesser degree by hydrophobic interactions, between the lactone ring of ascorbic acid and the pyranosic ring of the glucosamine unit of chitosan.

For the study of interactions of the chitosan (NF)-ascorbic system to pD/pH 5, the displacements of the system signals in relation to the isolated compounds were studied, observing a deformation of the chitosan signals, which were displaced to the field high in a manner consistent with what has been observed and described by Tian et al. (2009, Synthesis and Evaluation of Chitosan-Vitamin C complex. Indian J Pharm Sci. 71, 371-376). The presence of hydrogen bridge interactions with the antioxidant explains what is observed, since ascorbic acid is not in the nanofiber system.

Figure 18:
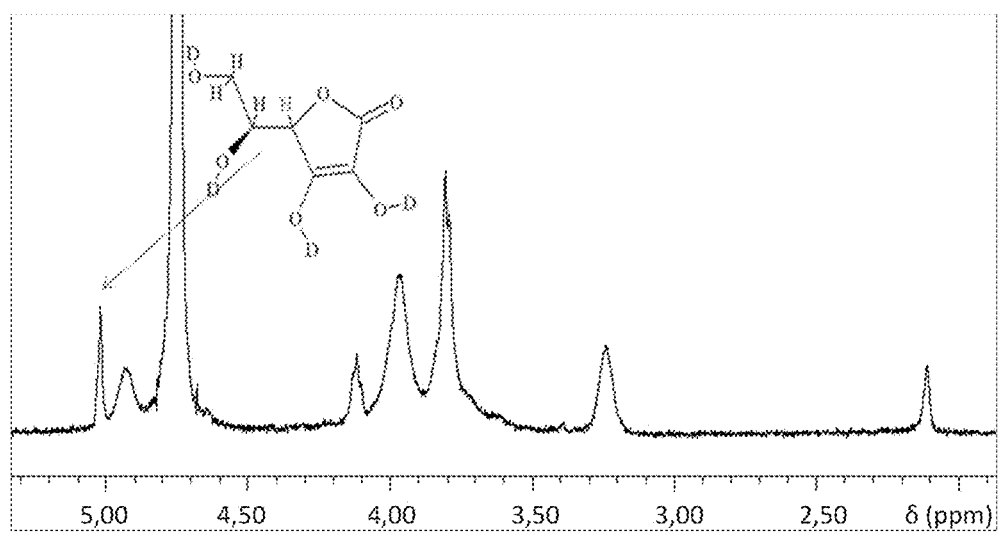
FIG. 18. NMR spectrum $^1$H of the chitosan-ascorbic acid system, in $D_2O$ at pD 1, and 37° C.

In the case of the chitosan-ascorbic system at pD/pH 3, the appearance of a low field signal at 5.03 ppm assignable to the proton $C_4$ of ascorbic acid was observed, showing a lower interaction with the polysaccharide when increasing the acidity. In the analysis of the interactions of the chitosan-ascorbic acid system at pH 1 (FIG. 18) it is possible to observe the ascorbic acid signals close to the behavior that it presented in an isolated form.

The results obtained show that the nanofibers of the invention form a system of chitosan and antioxidants stabilized through interactions (or bridges) of hydrogen, which disappear in the face of chemical stimuli, such as by increasing the acidity. Demonstrating that the main interaction that stabilizes the structure of nanofibers are the hydrogen bonding interactions, which confirms its functioning as a controlled release system and allows to explain its functioning under physiological conditions.

The preceding examples demonstrate the reproducibility of the invention by obtaining nanofibers with bioactive compounds of low molecular size, which have acid or lactone groups, aromatic and hydroxyl rings, in this case ascorbic acid and gallic acid and a mixture of these compounds, in this case a mixture of gallic acid, quercetin and ellagic acid. It also demonstrates the advantage of nanofibers over free antioxidants in vitro and in vivo. The scope of the present invention is defined in the appended claims.

The invention claimed is:

1. Nanofibers of self-assembled chitosan, consisting of:
   a. chitosan having a molecular size between 70 and 500 KDa and a degree of deacetylation between 65 and 90%, and
   b. bioactive compounds having a molecular size smaller than 0.5 KDa, which have acid groups, lactone groups, aromatic rings, hydroxyls, or a mixture thereof;
   wherein the nanofibers do not comprise covalent bonds between the chitosan and the bioactive compounds,
   the chitosan is present in an amount from 75% to 85% by mass relative to a total mass of the chitosan and the bioactive compounds,
   the bioactive compounds are present in an amount from 15% to 25% by mass relative to the total mass of the chitosan and the bioactive compounds,
   the nanofiber is stabilized by hydrogen bonds between the chitosan and the bioactive compounds, and
   the bioactive compounds are a mixture consisting of antioxidants gallic acid, quercetin, and ellagic acid.

2. The nanofibers of claim 1, wherein the chitosan has a low polydispersity molecular size.

3. The nanofibers of claim 1, wherein the nanofibers of the chitosan has a molecular size between 80 and 300 KDa.

4. The nanofibers of claim 1, wherein the chitosan has a degree of deacetylation between 75 and 85%.

5. A method of forming the nanofibers of claim 1, comprising mixing a solution of the chitosan with a solution of the bioactive compounds to form a solution mixture in a ratio of 3:1 to 4:1, shaking the solution mixture, and allowing spontaneous formation of the nanofibers.

6. The method claim 5, wherein the solution of the chitosan has a concentration of 0.5 to 1.5% m/v and the solution of the bioactive compounds has a concentration of 0.1 to 1.5% m/v.

7. A pharmaceutical or nutraceutical composition comprising the nanofibers of self-assembled chitosan according to claim 1.

8. The pharmaceutical or nutraceutical composition according to claim 7, wherein the nanofibers act as a controlled release system of the bioactive compounds.

9. The pharmaceutical or nutraceutical composition according to claim 7, wherein the pharmaceutical or nutraceutical composition is in a form for oral administration.

10. A method comprising administering the pharmaceutical or nutraceutical composition according to claim 7 to a subject, wherein the pharmaceutical or nutraceutical composition administers the bioactive compounds in different organs of the subject.

11. The method according to claim 10, wherein one of the organs is the brain.

12. The method according to claim 10, wherein the subject has a neurodegenerative disease.

13. The method according to claim 12, wherein the neurodegenerative disease is Alzheimer's, Parkinson's, Huntington's or Amyotrophic Lateral Sclerosis (ALS).

14. The method according to claim 11, wherein the subject has had an Ischaemic Stroke.

* * * * *

UNITED STATES PATENT AND TRADEMARK OFFICE
CERTIFICATE OF CORRECTION

PATENT NO. : 11,357,737 B2
APPLICATION NO. : 15/579886
DATED : June 14, 2022
INVENTOR(S) : Zuñiga et al.

It is certified that error appears in the above-identified patent and that said Letters Patent is hereby corrected as shown below:

On the Title Page

Item (73), in Column 1, in "Assignees", Line 4, delete "Valparaiso" and insert --Valparaíso--.

In the Claims

Column 18, in Claim 6, Line 11, delete "method claim" and insert --method of claim--.

Signed and Sealed this
Fifth Day of September, 2023

Katherine Kelly Vidal
*Director of the United States Patent and Trademark Office*